US006448468B1

(12) United States Patent
Surani

(10) Patent No.: US 6,448,468 B1
(45) Date of Patent: Sep. 10, 2002

(54) TRANSGENETIC MOUSE WHICH COMPRISES AN INACTIVE PEG3 GENE, AND THE USE THEREOF

(75) Inventor: Azim Surani, Cambridge (GB)

(73) Assignee: Cambridge University Technical Services Limited, Cambridge (GB)

(*) Notice: Subject to any disclaimer, the term of this patent is extended or adjusted under 35 U.S.C. 154(b) by 0 days.

(21) Appl. No.: 09/720,126

(22) PCT Filed: Jun. 25, 1999

(86) PCT No.: PCT/GB99/02009

§ 371 (c)(1),
(2), (4) Date: Dec. 21, 2000

(87) PCT Pub. No.: WO99/67407

PCT Pub. Date: Dec. 29, 1999

(30) Foreign Application Priority Data

Jun. 25, 1998 (GB) .............................. 9813778

(51) Int. Cl.[7] .......................... C12N 15/00; G01N 33/00
(52) U.S. Cl. .............................. 800/3; 800/18
(58) Field of Search ....................... 800/3, 18

(56) References Cited

PUBLICATIONS

L. Li, B. Keverne, S. Viville, S. Aparicio, S. Barton, F. Ishino and M.A. Surani; "Characterisation and Functional Analysis of the Imprinted Peg3 Gene In Mice" Br. Soc. Dev. Biol., Autumn Symp. 1997, Abst. # 57.

Frederic Relaix, Xiao–jun Wei, Xiangwei Wu and David A. Sassoon, "Peg3/Pw1 is an Imprinted Gene Involved in the TNF–NF$_k$B Signal Transduction Pathway"; Nature Genetics vol. 18 (1998) 287–291.

Joomyeong Kim, Linda Ashworth, Elbert Branscomb and Lisa Stubbs, "The Human Homolog of a Mouse–Imprinted Gene, Peg3, Maps to a Zinc Finger Gene–Rich Region of Human Chromosome 19q13.4"; Genome Res. 7 (1997) 532–540.

L.L. Li, E.B. Keverne, S.A. Aparicio, F. Ishino, S.C. Barton and M.A. Surani; "Regulation of Maternal Behavior and Offspring Growth by Paternally Expressed Peg3"; Science vol. 284 (1999) 330–333.

*Primary Examiner*—Michael C. Wilson
(74) *Attorney, Agent, or Firm*—Roylance, Abrams, Berdo & Goodman, L.L.P.

(57) ABSTRACT

The invention relates to the finding that animals deficient in the Peg3 gene suffer from a number of phenotypic traits, including obesity, aberrant thermoregulation and behavioral defects, including impaired maternal behavior. The invention provides a transgenic non-human animal which comprises an inactive copy for the Peg3 gene, and the use of such animals as model systems in assays for novel therapies in the treatment of conditions such as those mentioned above.

2 Claims, No Drawings

TRANSGENETIC MOUSE WHICH COMPRISES AN INACTIVE PEG3 GENE, AND THE USE THEREOF

The present invention relates to the Peg3 gene and the finding that it is involved in thermoregulation, obesity and maternal behaviour, olfaction, male behaviour, apoptosis, cell survival and degeneration, and infectious diseases.

The Peg3 gene was identified in a screen for expression of imprinted genes in mice. Imprinted genes show an unusual pattern of expression as their expression is determined strictly by their parental origin. Peg3 shows imprinting, with the paternal copy of the gene being expressed in offspring while the maternal copy is silent. The gene expresses an mRNA of about 9 kb in size which encodes an unusual zinc finger protein with eleven widely spaced "C2H2" motifs and two groups of amino acid repeats. The predicted size of the protein is 1,572 amino acids. See Kuroiwa et al, (1996), Nature Genetics 12; 186–189. The sequence of Peg3 can be found in GenBank, accession number AF038939 (NCBI-REF 363877).

Peg3 is expressed early in development in somites, branchial arches and other mesodermal tissue. In adults it is expressed predominantly in the brain including the hypothalamus medial preoptic area, amygdala as well as the olfactory bulb. It is also expressed in few other adult tissues such as the adrenal gland. The function of the gene is unknown, although in Kuroiwa et al, ibid, it is noted that the gene maps to a region of murine chromosome 7 which is syntenic with the human chromosomal location for genes associated with myotonic dystrophy and tumour suppression.

DISCLOSURE OF THE INVENTION

We have developed a transgenic mouse model in which we have disrupted the Peg3 gene. We have observed a number of surprising phenotypic changes, particularly obesity, lower core temperature, impaired maternal behaviour, abnormal male behaviour, smaller body size at birth and reduction in specific neurons in the hypothalamus. Moreover, obesity was found to develop in the mice despite a food intake lower than that of control animals. These findings suggest a role of Peg3 in the regulation of body weight and temperature, and provide a model system in which therapies for treatment of obesity, metabolic imbalances, growth regulation and behaviour may be studied.

The present invention thus provides a transgenic non-human animal, particularly a rodent, which comprises an inactive copy of the Peg3 gene.

The invention further provides a method of testing a putative modulator of body weight which comprises administering said putative modulator to an animal according to the invention and determining the effect of the putative modulator on body metabolism.

In an additional aspect, the invention also provides a method of testing a putative modulator of behaviour which comprises administering said putative modulator to an animal according to the invention and determining the effect of the putative modulator on behaviour.

The discovery of the function of the Peg3 gene allows the search for other genes involved in metabolic regulation, and thus the invention also provides a method for screening for genes associated with the regulation of body weight or temperature, which method comprises providing a Peg3 protein, bringing said protein into contact with other cellular proteins, and determining to which cellular proteins the Peg3 protein is able to bind. Such genes may be isolated and this forms a further aspect of the invention.

The role of Peg3 in mice allows the determination of a PEG3 genotype in humans with a phenotypic disorder associated with obesity or thermoregulation, by a method forming a further aspect of the invention. This method comprises:

providing nucleic acid from a group of obese patients and a control group of non-obese patients;

analysing said nucleic acid; and determining one or more features of said nucleic acid associated with the obese phenotype.

An analogous method may be performed at the protein level, using antibodies to determine epitopes of PEG3 which differ between groups, either in the relative strength of binding or in their presence or absence.

The differences in protein epitopes or genotype determined by such screening may be utilized to provide a method of testing an individual's susceptibility to obesity or a thermoregulatory disorder which comprises analysing the nucleic acid of said individual for one or more features of the PEG3 gene associated obesity or thermoregulatory disorders.

As used herein, "comprise(s)" and "comprising" are to be interpreted as "include(s) and "including".

DETAILED DESCRIPTION OF THE INVENTION

PEG3 Gene

The Peg3 which we have disrupted in mice is the gene whose sequence is given in GenBank accession number AF038939, (the disclosure of which is incorporated herein by reference) and which is located in mice in the proximal region of chromosome 7. However, reference herein to "Peg3" includes wild-type allelic forms of this gene in mice, as well as homologues found in other animals, including mammals such as humans. Reference to "PEG3" refers specifically to the human homologue of the gene and is used herein in reference to methods of diagnosis and the like practised on humans or samples from humans. The human PEG3 gene has been isolated and its partial sequence is available on the NCBI database (AB006625, Homo sapiens mRNA for KIAA0287 gene, partial ads). The 5' region, including the first exon (nucleotides 1–174), of PEG3 is also present in GenBank entry AC006115, and this shows high homology to the murine Peg3 sequence Genbank accession number AF105262, which, with AF105266, represent further Peg3 sequences. The complete sequence may be determined by using primers based on the database sequence as probes on cDNA libraries or to extend by PCR a mRNA source of the gene. The ESTs W49208 and W90868 (Database Est) provide additional murine Peg3 sources, and HS201228 and HS403225 (Database Est) provide additional human sources of PEG3 sequences.

A wild-type sequence is considered to be any sequence found in mice or other animals which are phenotypically normal as far as weight and temperature regulation are concerned.

Homologous sequences may be determined by routine methodology conventional in the art. Nucleic acid sequences encoding all or part of a Peg3 gene and/or its regulatory elements can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences.

For example PCR (polymerase chain reaction) cloning techniques will utilize a primers (e.g. of about 15–50 nucleotides) based on the sequence of murine Peg3 to a region of mRNA or genomic DNA encoding the mRNA which it is desired to clone. The primers will be brought into contact with the mRNA or DNA (for example obtained from a brain cell, particularly a fetal brain cell) or other embryonic or fetal tissues, a polymerase chain reaction under conditions which bring about amplification of the desired region will be performed and an amplified fragment will be isolated (e.g. by purifying the reaction mixture on an agarose gel). The primers may be designed to contain suitable restriction enzyme recognition sites so that the amplified DNA can be cloned into a suitable cloning vector.

Such techniques may be used to obtain all or part of a Peg3 gene from other animals, such as amphibians or mammals. Genomic clones containing a Peg3 gene and its introns and promoter regions may also be obtained in an analogous manner, starting with genomic DNA from a primary cell such as a liver cell, a tissue culture cell or a library such as a phage, cosmid, YAC (yeast artificial chromosome), BAC (bacterial artificial chromosome) or PAC (P1/P2 phage artificial chromosome) library.

Alternatively, homologues may be obtained by making or obtaining cDNA or genomic DNA libraries and probing such libraries with probes comprising all or part of the Peg3 murine gene under conditions of medium to high stringency (for example 0.03M sodium chloride and 0.03M sodium citrate at from about 50° C. to about 60° C.).

Generally, homologues will be at least about 60%, more preferably at least 70%, and even at least 80%, such as at least 90%, 95%, 98% or 99% homologous to murine Peg3 within the mRNA open reading frame. Mammalian homologues are particularly preferred.

The percentage homology (also referred to as identity) of DNA and amino acid sequences can be calculated using commercially available algorithms. The following programs (provided by the National Center for Biotechnology Information) may be used to determine homologies: BLAST, gapped BLAST and PSI-BLAST, which may be used with default parameters. The algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

"Inactive"

For the purposes of the present invention, it will be understood that reference to an inactive copy of the Peg3 gene includes any non-wild-type variant of the gene which results in an obese or hypothermic phenotype, or in behavioural disorders. Thus the gene may be deleted in its entirety, or mutated such that the animal produces a truncated protein, for example by introduction of a stop codon and optionally upstream coding sequences into the open reading frame of the Peg3 gene. Equally, the open reading frame may be intact and the inactive copy of the gene provided by mutations in promoter regions.

Generally, inactivation of the gene may be made by targeted homologous recombination. Techniques for this are known as such in the art. This may be achieved in a variety of ways. A typical strategy is to use targeted homologous recombination to replace, modify or delete the wild-type gene in an embryonic stem (ES) cell. An targeting vector comprising a modified Peg3 gene is introduced into ES cells by electroporation, lipofection or microinjection. In a few ES cells, the targeting vector pairs with the cognate chromosomal DNA sequence and transfers the desired mutation carried by the vector into the genome by homologous recombination. Screening or enrichment procedures are used to identify the transfected cells, and a transfected cell is cloned and maintained as a pure population. Next, the altered ES cells are injected into the blastocyst of a preimplantation mouse embryo or alternatively an aggregation chimera is prepared in which the ES cells are placed between two blastocysts which, with the ES cells, merge to form a single chimeric blastocyst. The chimeric blastocyst is surgically transferred into the uterus of a foster mother where the development is allowed to progress to term. The resulting animal will be a chimera of normal and donor cells. Typically the donor cells will be from a animal with a clearly distinguishable phenotype such as skin colour, so that the chimeric progeny is easily identified. The progeny is then bred and its descendants cross-bred, giving rise to heterozygotes and homozygotes for the targeted mutation. The production of transgenic animals is described further by Capecchi, M, R., 1989, Science 244; 1288–1292; Valancius and Smithies, 1991, Mol. Cell. Biol. 11; 1402–1408; and Hasty et al, 1991, Nature 350; 243–246, the disclosures of which are incorporated herein by reference.

Homologous recombination in gene targeting may be used to replace the wild-type Peg3 gene with a specifically defined mutant form (e.g truncated or containing one or more substitutions).

The inactive gene may also be one in which its expression may be selectively blocked either permanently or temporarily.

Permanent blocking may be achieved by supplying means to delete the gene in response to a signal. An example of such a means is the cre-lox system where phage lox sites are provided at either end of the transgene, or at least between a sufficient portion thereof (e.g. in two exons located either side or one or more introns). Expression of a cre recombinase causes excision and circularisation of the nuclei acid between the two lox sites. Various lines of transgenic animals, particularly mice, are currently available in the art which express cre recombinase in a developmentally or tissue restricted manner, see for example Tsien, Cell, Vol.87 (7): 1317–1326, (1996) and Betz, Current Biology, Vol.6 (10): 1307–1316 (1996). These animals may be crossed with lox transgenic animals of the invention to examine the function of the Peg3 gene. An alternative mechanism of control is to supply a promoter from a tetracyline resistance gene, tet, to the control regions of the Peg3 locus such that addition of tetracycline to a cell binds to the promoter and blocks expression of the Peg3 gene. Alternatively GAL4, VP16 and other transactivators could be used to modulate Peg3 expression including that of a transgene containing the Peg3 gene. Furthermore, Peg3 could also be expressed in ectopic sites, that is in sites where the gene is not normally expressed in time or space.

Transgenic targeting techniques may also be used to delete the Peg3 gene. Methods of targeted gene deletion are described by Brenner et al, WO94/21787 (Cell Genesys), the disclosure of which is incorporated herein by reference.

Another alternative is to insert into the Peg3 gene a vector which provides for the expression of a truncated wild-type gene through splicing of an exon mRNA to a splice acceptor site and on into non Peg3 gene sequence.

Reference may be made to the accompanying examples for the production of suitable transgenic mice in which the gene is disrupted by a vector comprising a marker gene and a stop codon. The Peg3 targeting vector used to illustrate the present invention contains (1) a splice acceptor site at the 5' end allowing the insertion of βgeo selection cassette within an intron;

(2) a translational stop codons in the three reading frames ensure premature translational termination of the targeted gene;

(3) an internal ribosome entry site (IRES) located upstream of βgeo allowing preferential translation reinitiation at the 5'AUG of βgeo in the fusion transcript independently of translation initiation at the endogenous gene (Mountford and Smith, Trends in Genetics II, 179–184, 1995);

(4) a promoterless βgeo gene consisting of an in-frame fusion between the bacterial genes lacZ and neo, coding for a bifunctional protein allowing both the selection of targeted clones and analysis of expression pattern of the targeted gene during development; and (5) an SV40 polyademethylation signal near the end of the cassette terminating transcription of the fusion gene.

Similar constructs may be made by those of skill in the art to provide vectors which achieve inactivation of the Peg3 locus. In one of the targeting constructs, the βgeo cassette is inserted downstream of the Peg3 translation start site at exon 3. This provides a truncated protein which may be detected in progeny. Analogous methods may be used in other mice or non-human mammals, including the use of other marker proteins, such as luciferase, chloramphenicol acetyl transferase and Green Fluorescent Protein.

PEG3-Expressing Transgenic Animals

In a further embodiment of the invention, there is provided a non-human animal which expresses Peg3 at a higher than wild-type type level. Preferably this means that the Peg3 gene is expressed at least 120–200% of the level found in wild-type animals of the same species, when cells which express the gene (e.g. the hypothalamus) are compared. Also, this gene could be expressed in an ectopic location where Peg3 gene is not normally expressed in time or space. Comparisons may be conveniently done by northern blotting and quantitation of the transcript level. The higher level of expression may be due to the presence of one or more, for example two or three, additional copies of Peg3 or by modification to the Peg3 genes to provide over-expression, for example by introduction of a strong promoter or enhancer in operable linkage with the wild-type gene. The provision of animals with additional copies of genes may be achieved using the techniques described herein for the provision of "knock-out" animals.

In another aspect, animals are provided in which the Peg3 gene is expressed at an ectopic location. This means that the gene is expressed in a location or at a time during development which does not occur in a wild-type animal. For example, the gene may be linked to a developmentally regulated promoter such as Wnt-1 and others (Echeland, Y. Et al., Development 120, 2213–2224, 1998; Rinkenberger, J. C. et al., Dev. Genet. 21, 6–10, 1997, or a tissue specific promoter such as HoxB (Machonochie, M. K. et al, Genes & Dev 11, 1885–1895, 1997).

Animals of this aspect of the invention may also be used as models in the development of assays for modulators of obesity, temperature regulation or behavioural disorders. Such animals may serve as additional control groups for assays of the invention which comprise an inactive Peg3 gene.

Non Human Animal

Non-human animals of the invention may be homozygous or heterozygous for the inactive Peg3 gene. Where heterozygous animals are used, it is preferred that the inactive (or otherwise modified for expression) gene is paternally inherited in the animal. This is because the maternal Peg3 gene is repressed and silent. However, heterozygotes in which the modified gene is maternally inherited also form part of the invention. Mammalian animals include non-human primates, rodents, rabbits, sheep, cattle, goats, pigs. Rodents include mice, rats, and guinea pigs. Amphibians include frogs. Fish such as zebra fish, may also be used.

Transgenic non-human mammals of the invention may be used for experimental purposes in studying obesity, thermoregulation or behavioural disorders, and in the development of therapies designed to alleviate the symptoms or progression of such conditions cause by a defect in the Peg3 gene. By "experimental" it is meant permissible for use in animal experimentation or testing purposes under prevailing legislation applicable to the research facility where such experimentation occurs.

Methods of Testing

The invention may be used in methods designed to assay putative modulators of weight, temperature regulation or behaviour. Generally, a test group of transgenic non-human animals of the invention will be tested in conjunction with a control group of animals of the same species-and preferably the same strain, which also have an inactive copy of the Peg3 gene, and optionally a control group of wild-type animals. The animals of all groups will be provided with a diet which may be hypo, hyper or iso-caloric, and the weight gain or loss of the test group measured and compared to suitable control groups. Usually, test animals are provided with surplus food, the intake of which may then be determined by measuring the difference between the food provided and food remaining after a period of time.

The putative modulator may be any candidate substance which may be involved in regulation of weight, temperature or behaviour. For example, candidate substances include hormones or other peptides (including for example leptin, insulin, thyroid, hormone, TNF),(Huang, Q. Et al., Endocrinology 139, 1524–1532, 1998; Hwang, C. S. et al., Ann. Rev. Cell. Dev. Biol. 13,231–259,1997), prostaglandins, synthetic or naturally occurring chemical compounds, for example extracts of plants, steroids, benzodiazapenes, dexfluoroamphetamines or other amphetamine derivatives (Popovich, N. G. et al., J. Am.Pharm.Assoc.Wash., 37,31–39,1997). Compounds may be administered to test animals by any suitable route, for example orally or by intravenous injection, although other routes (e.g. buccal, nasal, transdermal, rectal, etc, are not excluded). The dose of a putative modulator will depend upon its nature and potency, and may be determined by those of skill in the art taking into account the nature of the test substance.

In a preferred aspect of the invention, test animals will be used in the assay of putative modulators of weight. However, the study of the other phenotypic effects of Peg3 knockout will also be useful. For example, the putative modulators which restore proper thermoregulation, or alleviate the reduction in temperature, (Gong et al., J. Biol. Chem. 26, 24129–24132,1997) may be useful in treating conditions such as hypothermia or pyrexia of any origin, for example pyrexia due to endotoxin stimulus during infection, (Doig, G. S. et al. Crit. Care. Med. 25, 1956–1961, 1997) pyrexia associated with cell necrosis or hypespyrexia as a consequence of halothane or other drug administration (Kim, S. H. et al. J. Trauma 44, 485–491, 1998).

Additionally, the phenotypic effects on behaviour, particularly maternal behaviour, may be used as a determinator in the development of drug therapies for depression including post-natal depression or other behavioural disorders. The phenotypic effects may also be used in the development of therapies for modifying olfaction, cognition and male behaviour.

In a further aspect the invention provides transgenic animals with an inactive or modified Peg3 gene. Manipulation of Peg3 function or the administration of weight regulatory compounds to such transgenic animals may provide alteration in the ratio of fat to muscle in domestic livestock.

In a further aspect of the invention we have observed that in the preoptic nucleus of the hypothalamus, significantly fewer oxytocin containing neurons are found in our transgenic animals as opposed to control animals. This suggests that either these neurons have never formed or that, importantly, they may have degenerated by one of several processes. Peg3 may therefore be important in the control of cell death or degeneration, particularly in the nervous system. Accordingly, the present invention provides transgenic animals in methods of testing compounds with the ability to enhance or repress degeneration of neurons in the brain or other tissues. Measuring the activity, amount or integrity of Peg3 may also act as a diagnostic or staging test for diseases involving cell death and degeneration, such as Alzheimers disease. Furthermore, compounds which alter cell degeneration via the Peg3 pathway may be used in methods of treatment of cancer.

Accordingly, in a further embodiment of the invention transgenic animals may be used in a method of testing the potential carcinogenicity of compounds by administering a test compound to a transgenic animal of the invention and determining whether said animal has an increased risk of tumour development compared to non-transgenic controls and/or untreated transgenic controls.

Animals of the invention may also be used as recipients of xenografts, particularly xenografts of human tumour cells. The efficacy of candidate anti-tumour compounds may then be tested in such transgenic animals to analyse the mode of action of the test compound and determine whether said mode of action is via a pathway regulated by or requiring Peg3.

Gene Screening

The identification of Peg3 as a regulator of weight, temperature and behaviour provides a means to identify further genes which may interact with Peg3 to regulate the observed phenotypes. Thus the invention provides assay methods and means to achieve this. Generally, such assays are based upon detecting the interaction at the protein level of the Peg3 protein with other proteins.

One way to achieve this is by using a two hybrid screening assay. Two-hybrid assays may be in accordance with those disclosed by Fields and Song, 1989, Nature 340; 245–246. In such an assay the DNA binding domain (DBD) and the transcriptional activation domain (TAD) of the yeast GAL4 transcription factor are fused to the first and second molecules respectively whose interaction is to be investigated. A functional GAL4 transcription factor is restored only when two molecules of interest interact. Thus, interaction of the molecules may be measured by the use of a reporter gene operably linked to a GAL4 DNA binding site which is capable of activating transcription of said reporter gene. Other transcriptional activator domains may be used in place of the GAL4 TAD, for example the viral VP16 activation domain. In general, fusion proteins comprising DNA binding domains and activation domains may be made.

In the present case polypeptides of the invention may be expressed as fusion proteins with an appropriate domain and candidate second polypeptides with which those of the invention might associate can be produced as fusion proteins with an appropriate corresponding domain. This may be carried out in suitable cells, such as yeast, insect or mammalian cell lines. Alternatively libraries such as phage display libraries of such fusion proteins may be screed with a fusion polypeptide of the invention.

The use of a two-hybrid approach allows isolation of the gene (or at least a portion thereof which may be used to clone the whole gene) encoding the protein which interacts with Peg3 protein.

An alternative approach is an immunoprecipitation. Antibodies against Peg3 may be made, and used to immunoprecipitate this protein from cells in which it is produced, under conditions wherein a protein associated with Peg3 co-precipitated. The protein may be analysed by traditional protein chemistry, and primary sequence used to design probes to clone it. Alternatively, the primary sequence data may be compared against EST databases for candidate genes.

Isolated sequences of nucleic acids obtainable in this way form a further aspect of the invention.

PEG3 Genotypes

The finding that Peg3 is associated with the phenotypic disorders mentioned herein allows the development of genetic markers to determine the susceptibility of an individual to obesity or other disorders. Thus in a further aspect of the invention, the Peg3 gene from obese subjects, including human subjects, may be analysed, compared to the gene found in non-obese subjects. In the case of human subjects, obese individuals are preferably those with a body mass index (b.m.i., calculated as weight (kg) divided by height (m) squared) of over 25, and preferably over 30.

Nucleic acid—e.g mRNA from cells expressing Peg3 or DNA from any cells may be analysed by any suitable means for detecting variation in individuals. Suitable methods include determining restriction fragment length polymorphisms (RFLPs), PCR product polymorphisms (i.e. the length of an amplified region of the gene produced using a primer pair), direct sequencing of all or part of the gene, or heteroduplex analysis. One or more of these methods may be used to determine features in the Peg3 gene of obese individuals which is associated with obesity. Similarly, associations with other disorders may be determined.

The association need not be one which is found in 100% of obese subjects and 0% of non-obese subjects. Predictive markers for phenotypic traits may be those which are found at a higher frequency in the subject population than in controls. Thus markers may be developed which indicate an increased risk of obesity or other Peg3-deficient-associated traits, so that individuals at risk may be treated before symptoms occur.

In an analogous manner, individuals showing symptoms of any of the disorders we have found to be associated with Peg3 inactivation may be screened for Peg3 protein, for example using antibodies against the protein. Antibodies may be obtained using techniques which are standard in the art. Methods of producing antibodies include immunising a mammal (e.g. mouse, rat, rabbit) with a polypeptide of the invention. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies according to the present invention may be modified in a number of ways. Indeed the term "antibody" should be construed as covering any binding substance having a binding domain with the required specificity. Thus the invention covers antibody fragments capable of binding an antigen or other binding partner such as an Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Antibodies may be made against epitopes of the Peg3 protein, and differences in binding of the antibodies to body samples from obese individuals (or those who are hypothermia or suffering from a behavioural disorder) and control individuals compared to determine an epitope whose binding differs between the two groups.

The identification of nucleic acid or protein markers of the Peg3 gene associated with obesity, temperature regulation, behavioural disorders, apoptosis, cell survival or resistance to infectious diseases provides a further aspect of the invention. Diagnostic methods and markers may be used on samples from individual subjects, to determine that individual's own risk of developing the one of these conditions, or the prognosis for treating the condition. For example, where particular polymorphisms such as deletions, truncations or substitutions of the wild-type Peg3 gene are found to be associated with one of these conditions, then a nucleic acid probe may be prepared to detect the presence or absence of the particular polymorphism.

Tests for detecting nucleic acid generally comprise bringing a human or animal body sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected. Suitable assay methods of this any other formats can be found in for example WO89/03891 and WO90/13667.

Probes used in such techniques may be in the form of a short probe (for example of 15 to 50, such as 18 to 24 nucleotides) which is capable of hybridising to the wild-type sequence and not to the disease associated sequence, or vice versa. The probe may be packaged in a kit with suitable control reagents, instructions, and the like.

In another embodiment, the sample nucleic acid may be in the form of whole chromosomes, for example as a metaphase spread. The nucleic acid probe or primer of the invention may be labelled with a fluorescent label to detect the chromosomal location of a Peg3 gene in the spread.

Similarly, antibodies which are capable of binding diagnostically significant epitopes of Peg3 may likewise be packaged in a kit with controls, instructions, and the like. Immunoassay methods are well known in the art and will generally comprise:

(a) providing an antibody capable of binding an epitope of Peg3;

(b) incubating a biological sample with said antibody under conditions which allow for the formation of an antibody-antigen complex; and (c) determining whether antibody-antigen complex comprising Peg3 is formed.

Peg3 Therapeutics

The identification of a role for Peg3 in the above described manner provides a novel target for therapeutic agents. Modulators of Peg3 obtained by assay methods of the invention may be used to treat a variety of conditions, including, for example, depression, imparied maternal care, abberant thermoregulation and obesity. The latter, in the form of late onset obesity, can occur with ageing, partly due to changes in energy balance and a lack of thermoregulation and thus Peg3 forms a target linking the two and may be critical to devising appropriate treatments for such conditions.

The identification of Peg3 alleles or polymorphisms in human populations associated with obesity will provide a means to identify individuals at risk of obesity at an early stage, and thus provide appropriate treatment or the introduction of lifestyle changes which may reduce the effect of a risk-associated allele or phenotype.

The invention is illustrated by the following examples.

Materials and Methods

Construction of Targeting Vectors

Peg3 genomic clones were isolated from two phage libraries, λKO and λPS (Nehls, 1994) of mouse strain 129/Sv using Peg3 cDNA clones as probes. The DNA insert of the phages was excised in the plasmid form (in pKS+) after infection of cre recombinase-expressing E. coli strain BNN132. The structure of the Peg3 gene was partially established; the putative open reading frame begins at exon 3 and all the zinc finger motifs are encoded by the last coding exon 9 (Li, 1997). A genomic clone pB* spanning exons 3 to 9 of Peg3 was used as the backbone of the targeting vector. A 4.8 kb XhoI-fragment of the IRES-βgeo selection cassette from pIFstop was inserted into the XhoI site of pB* in the same transcriptional orientation as Peg3 to generate the Peg3$^{\beta geo}$ targeting vector.

Electroporation and Screening of ES Cell Clones

ES cells were manipulated mainly as described (Robertson, 1987 Joyner, 1993). R1 ES cells (Nagy, 1993) were cultured on feeder layers of mitomycin C-treated primary embryonic fibroblasts (PEFs) in ES/LIF medium at 37° C. with 6% $Co_2$. 50 μg of NotI-linearized targeting vector was electroporated into $10^7$ ES cells in 1 ml of the culture medium at 125 μF and 250 V. Subsequently, the cells were cultured on NeoPEF feeders in ES/LIF medium for one day, followed by selection in the presence of 150 μg/ml G418 for 10 days. Resistant clones were grown and expanded in duplicate in 24-well plates, one to obtain frozen stocks and the other to prepare DNA for Southern analysis.

Generation of Chimeric, Heterozygous and Homozygous Mice

The targeted ES clones were karyotyped (Tada, M. Et al. EMBO J. 21, 6510–6520, 1997). and injected into 2.5 dpc MF1 (or C57BL/6J) blastocysts, which were transferred to pseudopregnant females. Chimeric male progeny were bred with MF1 (or C57BL/6J) females and germline transmission was recognised by the agouti coat colour in the offspring. Heterozygotes inheriting the mutated allele from the father were detected by β-gal staining of their tail buds or yolk sac membrane (for embryos) or toes (for neonates at 10 dpp) or Southern analysis of DNA. Progeny from intercrosses of heterozygotes were genotyped by a combination of β-gal staining and either Southern or PCR analysis of DNA.

Southern and Northern Analysis

Genomic DNAs were isolated using Proteinase K/SDS lysis solution as described (Hogan et al., 1994). Total RNA from embryos or ES cells was prepared using the Gibco BRL TRIzol® reagent and Poly A$^+$ RNA was purified using the Qiagen Oligotex™ direct mRNA kit. Northern and Southern analysis was performed based on standard protocols (e.g. Sambrook et al. 1992 cited above).

Reverse Transcription-polymerase Chain Reaction (RT-PCR) and PCR

The reverse transcription reaction was performed using 0.5–1 μg of total RNA in a 20 μl volume containing 1.0 μM random hexamer primers, 1.0 U/μl RNase inhibitor, 1×reaction buffer, 0.5 mM DNTP and 10.0 U/μl MMLV reverse transcriptase (Clontech) at 42° C. for 1 hr. PCR was performed using 1 ml of reverse transcription products or 1/2500 volume of tail DNA (1 cm length at 10 dpp) in a 50 ml reaction containing 1×PCR buffer, 200 mM dNTP, 0.5 mM each primer and 0.05 unit/ml Taq DNA polymerase (Boehringer Mannheim). The reaction was subjected to a denaturation step (3 min at 93° C.), 30 or 35 cycles [30 sec at 93° C., 30 sec at (primer's Tm–5)° C., and 1 min/per kb of the length of PCR-products at 72° C.] and a final extension step (5 min at 72° C.). The following primers are used:

Histology and Histochemical Analysis

Embryos or tissues were fixed in 4% formaldehyde/PBS at 4° C. for overnight (for routing histology) or few hours (for cryosection β-gal staining and immunohistochemistry).

Whole Mount β-gal Staining

Embryos and tissues were fixed in the fixative solution (2% formaldehyde, 0.2% glutaraldehyde, 0.02% NP-40, 1 mM MgCl$_2$ and 0.24 mM sodium deoxycholate in PBS) for 1–2 hr at 4° C. and stained with β-gal staining solution (1 mg/ml X-gal, 4 mM K$_4$Fe(CN)$_6$-3H$_2$O, 4 mM K$_3$Fe(CN)$_6$, 2 mM MgCl$_2$ and 0.02% NP-40 in PBS) at 30° C. in the dark until the colour developed. The embryos were postfixed in 4% formaldehyde in PBS at 4° C., dehydrated and stored in 70% ethanol.

Cryosection β-gal Staining

Fixed tissues were equilibrated in 30% sucrose in PBS at 4° C. overnight and frozen on dry ice. The 15 mm-thick cryosections were stained with β-gal staining solution, postfixed and counter-stained with eosin or nuclear fast red.

Immunohistochemistry

Immunostaining was performed using the Vectastain® ABC Elite kit. Sections were postfixed in 4% formaldehyde in PBS, digested with 0.25% trypsin for 5 min at room temperature and blocked with the ABC blocking solution for 1 hr. The sections were incubated with polyclonal antibodies against mouse prolactin (UCB), mouse growth hormone (UCB) or adrenocorticotropic hormone (ACTH 1–24) (Biogenesis) 1000-fold diluted in the ABC blocking solution, 0.3% Triton X-100 and 0.2% NaN$_3$ at room temperature overnight. The antibodies were detected using the biotinylated goat anti-rabbit IgG/avidin DH-biotinylated horseradish peroxidase H/DAB-NI system. Before incubating with avidin DH-biotinylated horseradish peroxidase H, the sections were treated with 0.3% H$_2$O$_2$ in methanol at 30 min to inactivate endogenous peroxidase. Finally, sections were dehydrated and mounted in DPX.

Maternal Behaviour Analysis

Three groups of females, virgin females aged 50–60 days, newly postpartum primiparous females and cycling multiparous females, were tested for maternal behaviour (Yeo and Keverne, 1986). For the postpartum females, their own pups were temporally removed from cages. Three newborn pups were separately placed opposite to the nest site of each female tested in the cage and nest materials were moved to the centre of the cage. The responses of females as described below were recorded for the following 30 min. (1) Retrieving: the female picked up a pup and transported it to her nest site. (2) Nest building: the female brought nest materials to her nest site. (3) Crouching over pups: the female covered over the 3 pups and arched her back in a nursing posture. The times to retrieve the first pup (latency to retrieve) and all 3 pups (retrieval time), to exhibit nest building (latency to nest build) and to exhibit crouching over the pups (latency to crouch over) were recorded.

Male Sexual Behaviour

To test for male sexual behaviour, individual mutant or control virgin males were tested with females in oestrous in a standard 15 minute interaction test. Alternatively, individual control and mutant virgin males were introduced into a large cage with five females of which only one was at oestrous. The ability of males to dect this female and to initiate sexual behaviour was monitored.

Body Weight and Feeding Analysis

For this experiment, animals were housed singly to avoid competion between animals, under standard animal house conditions: temperature, t21°±1° C. with 15 air changes/hr. Reverse lighting (light on 1900 hr, lights off 0700 h). Each animal received 100 gm Expanded Diet. Food was always in surplus. Each animal received 100 gm RM3 expanded diet. At weekly intervals the remaining food was weighed and replaced with further 100 gm of food. The average consumption was found to be 27–35gm/week/mouse. At this weekly intervals, animals were weighed and their rectal temperature was recorded at 09.00 h each week. The control and mutant males were matched for age which was 17 months. They were monitored over a 16 week period.

Results

Targeting of the Peg3 Gene

RT-PCR analysis indicated that Peg3 is expressed in ES cells. To disrupt the Peg3 gene and simultaneously follow its expression pattern, the Peg3$^{\beta geo}$ targeting vector was constructed, which contains a promoterless IRES-βgeo selection cassette inserted in exon 5 of Peg3. The internal ribosome entry site (IRES) allows the preferential translational initiation at the 5' AUG of βgeo in the fusion transcript (Mountford and Smith, 1995). This cassette consists of the translation stop codons in three reading frames at the 5' end and SV40 polyadenylation signal at the 3' end to terminate expression of the endogenous and fusion genes, respectively. The linearized targeting vector was electroporated into R1 ES cells (Nagy et al., 1993). 17 out of 68 (25%) G418-resistant clones were detected as homologous recombinants by Southern analysis with a 5' and a 3' external probe. The single-copy replacement of the targeting construct was confirmed using a 5' fragment of βgeo. The high frequency of homologous recombination obtained reflected the selective enrichment from both the promoter trap and IRES function.

Generation of Peg3$^{\beta geo}$ Mutant Mice

Two clones with normal chromosome number were injected into MF1 blastocysts and another four, into C57BL/6J blastocysts. Male chimeras were bred with MF1 (or C57BL/6J) females. Male chimeras with 100% germline transmission were mated with 129/Sv females to establish the Peg3$^{\beta geo}$ allele on an inbred genetic background. As Peg3 expression is of the paternal allele only (Kuroiwa et al., 1996, ibid), it is expected that the Peg3$^{\beta geo}$ mutation phenotype and lacZ expression will be detected after paternal transmission of this allele. (Hereafter, heterozygotes inheriting Peg3$^{\beta geo}$ from the father or mother are referred to as +/− or −/+ mice, respectively.) The +/− mice were identified by β-gal staining of toes or Southern analysis of tail DNA. They were smaller and recovered at the expected Mendelian ratio (50%). Furthermore, intercrossing of +/− mice segregated four genotypes (+/+, +/−, −/+ and −/−) approximately in a ratio of 1:1:1:1. Expression of Peg3 in Peg3$^{\beta geo}$ mutant embryos was examined by Northern analysis using a Peg3 cDNA probe which hybridises to a region 3' of the βgeo insertion site. In the +/+ and −/+ embryos with an intact paternal copy, the 9 kb full length Peg3 mRNA was clearly detected. In contrast, there was no or little transcript in +/− and −/− embryos. The same membrane was reprobed with human GAPDH cDNA to confirm approximately equal amounts of the four samples used. On the other hand, a 5' fragment of the βgeo cassette hybridised to a major 5–6 kb transcript only in +/− and −/− mutant embryos. The size of this transcript agreed with the expected Peg3$^{\beta geo}$ fusion transcript terminating at the SV40 polyadenylation site at the 3' end of the βgeo cassette. Further RT-PCR analysis detected aberrant Peg3$^{\beta geo}$ transcripts in the +/− mutant embryos: one amplified by the primer pair specific to exons 4 and 6 of Peg3 and flanking the βgeo insertion site and the other, by the primer pair specific to neo and exon 6 and flanking the 3' integration site of βgeo. DNA sequencing revealed that the former deletes most of the βgeo cassette and exon 5 and the latter lacks the 3' half of exon 5 both due to alternative splicing. Nevertheless, both transcripts contain translation stop codons within the Peg3 open reading frame, which begins at exon 3. At the present time antibodies against the C-terminus of the Peg3 protein was not available and therefore we cannot prove whether Peg3$^{\beta geo}$ acts as a true null allele or as a hypomorph. But Peg3 function must be impaired because of the dramatic reduction observed in its transcription.

Expression of Peg3$^{\beta geo}$ During Mouse Development

Expression of lacZ was examined in Peg3$^{\beta geo}$ +/− heterozogotes at various developmental stages by whole mount and or cryosection β-gal histochemical staining. Wild-type samples were stained in parallel and, unless specified below, none displayed β-gal activity.

Expression of lacZ During Embryogenesis

β-gal activity was first detected weakly in the extraembryonic tissues of 6.5 dpc early postimplantation embryos. Later, the staining was apparent in the yolk sac, amnion and chorion membranes and allantois, which persisted throughout the rest of gestation. In 7.5 dpc embryos, β-gal activity was noted in the head fold ectoderm, lateral mesoderm and primitive streak. A similar pattern was observed for expression of Peg3 mRNA by whole mount in situ hybridisation. At 8.5 dpc, β-gal staining was strong in the prospective gut regions, weak in the somites and absent in the neural tube. At 9.5 and 12.5 dpc, the staining pattern corresponded well to the expression pattern of Peg3 mRNA described previously by Kuroiwa et al, 1986, ibid; a high level of activity was primarily located in mesoderm and endoderm derived tissues such as the developing gut and skeleton. Additional sites with lacZ expression were the limb buds, optic and auditory vesicles and surface ectoderm.

Expression of lacz During Postnatal Life

The expression pattern of lacZ in neonates was similar to that in embryos, while the pattern changed largely by the adult stage. β-gal staining was strong in the tongue, rib, intercostal muscle and intestinal wall of the neonates but the signals declined or retained only in a subset of cells in adults. A weak endogenous β-gal activity was found in the wild-type neonatal gut. Except for the regions including the hypothalamus, where Peg3 is known to be highly expressed (Kuroiwa et al., 1996), the brain showed a relatively low level of β-gal activity in neonates. However, the activity increased by the adult stage. A strong β-gal signal was also detected in the atrium of the heart, the intermediate and anterior pituitary and the adrenal medulla and the staining patterns persisted during postnatal life. No β-gal staining was observed in the thymus, spleen and liver.

Growth Reduction of Peg3$^{\beta geo}$ mutants

Peg3$^{\beta geo}$ +/− mice were smaller than their sex-matched wild-type (+/+) littermates. They were proportional dwarf as revealed by relatively reduced weight in their organs (and carcass). To determine when their growth was affected, the litters from (+/+×+/−) crosses were weighed at 1, 10 and 30 dpp. At 1 dpp, the +/− mutants were 80–85% of normal weight. This ratio remained relatively constant on the MF1/129/Sv or C57BL/6J/129/Sv mix backgrounds but declined to 65% on the 129/Sv inbred background by the time of weaning. However, the 129/Sv adult mutants caught up with 80–85% of normal weight. The litters from (+/−×+/−) crosses on the MF1/129/Sv background were also analysed. With respect to growth rate, the paternal heterozygotes (+/−) were similar to homozygotes (−/−), while the maternal heterozygotes (−/+) were indistinguishable from wild-type mice (+/+); the former group were smaller than the latter group. Further examination during embryogenesis showed that the growth retardation of the +/− embryos was apparent (8%) at 16 dpc but significant (15%) at 18 dpc. In addition, their placentas were 20–30% smaller at these two stages. These results show that paternal transmission of Peg3$^{\beta geo}$ caused foetal and placental growth retardation, plus postnatal growth retardation when on the inbred background.

Impaired Maternal Behaviour in Peg3$^{\beta geo}$ Mutant Females

Strikingly, all the pups from initial crosses between 129/Sv +/− mutants died within a few days, which was not observed on a mix background. The pups were born intact and could be rescued by foster mothers, suggesting a problem with the +/− mutant mothers. Therefore, the mutant females were compared with their wild-type siblings, respectively, mated to the mutant males in respect of nurturing ability (Table 1, +/−×+/− vs +/+×+/−) 10 out of 12 (83%) wild-type females raised their first litters and 68% of their progeny grew to weaning. By contrast, only 1 out of 12 (8%) first litters and 7% of the pups born to the mutant females survived. The 10 fold decrease in pup survival rate argued that the phenotype was attributed to the Peg3$^{\beta geo}$ mutation, rather than to an effect of the 129/Sv poor breeder strain. Similar results were obtained for 5-month-old females when mated to wild-type males (Table 1, +/−×+/+ vs +/+×+/+); only 1 out of 8 mutant females nursed their first litters compared to the majority (6/7) of wild-type females. This confirmed that the pup death was caused by the mutant mothers, as it occurred even in the absence of the mutant father and pups (Peg3$^{\beta geo}$ is silent after maternal transmission) and showed that the nurturing defect in the mutant females was irrespective of their size. Nevertheless, their nurturing ability improved with increased number of parturition; 50% (5/10) of the mutant females showed nurturing ability at the second parturition and 70% (7/10), at the third parturition. It is known that rodent pups, born immature, require considerable maternal care including, for example, providing a warm nest, retrieving pups into the nest, crouching and nursing to survive (Numan, 1994a). In contrast to newborn pups normally groomed by mothers, those born to the primiparous Peg3$^{\beta geo}$ mutant females were found to be scattered around in the cages, indicating the lack of maternal care. We therefore tested maternal behaviour of the primiparous postpartum mutant (+/−) and wild-type females towards three newborn pups. The wild-type females retrieved the first and all pups within 28±11.6 sec and 190±107 sec, respectively. By contrast, the mutant females spent approximately 11 and 3 fold time, respectively, to undertake and complete the behaviour. After 97.8±58 sec of presentation of pups the wild-type females began to build a nest, whereas the mutant females displayed an 8 fold longer latency. The mutant females never exhibited the onset of crouching over the pups during the 900 sec of testing, while the wild-type females did after 390±121 sec. Their impaired maternal responsiveness was not due to a failure in observing pups, since they sniffed them as much as wild-type females. Non-pregnant mice also show maternal behaviour although their responsiveness is not as immediate as that in postpartum females (Numan, 1994a). To address whether the Peg3$^{\beta geo}$ mutation affects maternal behaviour outside the context of parturition, virgin and multiparous cycling females were examined. Consistent with the fact that prior maternal experience facilitates the expression of maternal behaviour (Numan, 1994a), the multiparous females (maternal experience) showed a latency intermediate between the virgin and postpartum females in most of the measures on both the wild-type and Peg3$^{\beta geo}$ +/− backgrounds. Importantly, when the two genotypes were compared, the mutant females with or without experience both spent a significantly longer time to retrieve all pups and to exhibit nest building. Although these cycling females seldom crouched over the pups within the test time, most (5/6) of the multiparous wild-type females showed this behaviour after 1.5 hour of exposure to the pups, whereas few (1/6) of the multiparous mutant females did so. Taken together, the results showed that the Peg3$^{\beta geo}$ mutant females were less maternal than wild-type females regardless of parturition.

TABLE 1

Nurturing defects in Peg3$^{Bgeo}$ +/− and −/− females.

| Mother | Father | Number of mothers feeding pups (a) parturition | | | Number of pups surviving parturition | |
|---|---|---|---|---|---|---|
| | | 1st | 2nd | 3rd | 1st | 2nd |
| +/− | +/− | 1/12 | 5/10 | 7/10 | 4/56 | 20/56 |
| +/+ | +/− | 10/12 | 10/12 | | 67/99 | 70/84 |
| +/−* | +/+ | 1/8 | | | | |
| +/+* | +/+ | 6/7 | | | | |
| −/− | +/+ | 0/7 | | | | |
| −/+ | +/+ | 4/5 | | | | |

(a) Mice were scored for the ability to feed at least one pup to weaning
*Females aged 4–5 months when used for mating.

Their impaired maternal responsiveness at postpartum may contribute to the pup death.

An impaired maternal responsiveness in the Peg3$^{\beta geo}$ mutant females correlated with strong Peg3 expression in the adult brain promoted us to investigate further the expression pattern of Peg3 in brain. Expression of Peg3 mRNA, which was widely distributed in brain regions, was observed strongly in the hypothalamic nuclei, including the medial preoptic area (MPOA) as well as in the limbic system, for example, medial amygdala, bed nucleus stria, hippocampus and dentate gyrus. Studies such as lesion and knife cut experiments showed clearly the involvement of these regions in maternal behaviour (Numan, 1994b). This expression pattern of Peg3 observed here suggests that the gene may act on those regions to affect maternal behaviour.

One of molecular markers used to map the neural circuits implicated in maternal behaviour is the Fos gene family, as the members of this family such as c-Fos and FosB are activated in the MPOA of postpartum females or virgin females induced to be maternal after exposure to pups (Brown et al., 1996; Calamandrei and Keverne, 1994). In addition, mice deficient for FosB showed an impaired maternal behaviour (Brown et al., 1996) . We then examined whether the FosB-positive activated neural circuits are normal in Peg3$^{\beta geo}$ mutants. Immunostaining with FosB antibody showed that FosB-positive neural cells are increased in the virgin mutants after exposure to pups at the level comparable to that in the wild-type. Thus this neural circuit appeared not to be affected by Peg3$^{\beta geo}$ mutation. Unlike FosB induction, β-gal staining of mutant brain cryosections displayed a pattern similar to that of Peg3 expression and, no obvious change after pup-directed maternal responsiveness. Besides, no gross anatomical abnormality in mutant brains was observed during these studies.

Reduced Xxytocin-producing Cells in Peg3$^{\beta geo}$ Mutant Mothers

The pups sired by the mutant females were found to gain less weight during the feeding period, compared to those sired by wild-type females. This could result from the impaired maternal reponse (described above) and/or a latating problem in the mutant females. To investigate these possibilties, we measured weigh gain of pups born to these females. Following 2 hr separation from the pups, the mutant mothers were slower to adopt the behaviour of crouching over than wild type mothers (15.3 vs 8.7 min, p<0.004). The pups sired by the wild type females increased weight after 6 hr and after 24 hr. In contrast, those sired by the mutants gained no weight after 6 hr and only after 24 hr. Since all the pups attached the nipples 1 hr after separation, the failure to gain weigh in later group must be attributed to the latating problem in the mutant females.

The mutant females seemed to have relatively normal mammary glands, as ajuged by their histological morphology at both prepartum and postpartum. Milk ejection depends on both the sucking stimulation form the pups and the function of oxytocin. They were found to have fewer oxytocin-expressing cells in their hypothalamus compared to wild-type females by immunostaining.

Male Sexual Behaviour

Pairing male and oestrous female in a standard 15 minute interaction test revealed no significant difference between Peg 3 males and 129 controls. However, introducing a virgin male into a large cage of five females with only one them in oestrus, produced significant differences in the behaviour of mutant males compared with the 129 controls. The mutant males showed interest in females but they were much slower at identifying the oestrous female and initiating sexual behaviour.

Latency to Mounts (Mins)

Mutant males 11.58±0.96 t=2.53 df10

Control male 8.03±1.02 p<0.02

Body Weight and Feeding

The total food consumption, weight gain and rectal temperature were examined in groups of transgenic mice and controls. The control (5 animals) and mutant group (6 animals) of animals were matched for age and sex (male) (17 months). They were monitored over a period of 16 weeks. Their weight, food consumption and rectal temperatures were observed at weekly intervals. This resulted in a marked weight gain compared to the control group (p>0.003) while at the same time the food consumption by the mutant animals was lower than that observed in the control animals. The core (rectal) temperature of the mutant mice was also significantly lower than that observed in the control animals (p>0.005).

REFERENCES

Nehls, M., et al (1994) Biotechniques 17, 770–775

Li, E., et al (1993) Nature 366: 362–365

Robertson, E. J., (1987) Teratocarcinoma and embryonic stem cells: A practical approach., IRL, Oxford University Press, UK Joyner, A. L., Ed (1993) Gene targeting. A practical approach. IRL Press, Oxford University Press, Oxford, UK Nagy, A., et al (1993) *Proc. Natl. Acad. Sci. USA* 90, 8424–8428

Hogan, B., et al (1994) Manipulating the mouse embryo. Cold Spring Harbor Laboratory Press, New York Yeo, J. A. G. and Keverne, E. B., (1986) Physiol-Behav.37, 23–26

Mountford, P. S. and Smith, A. G., (1995) Trends-Genet. 1995:11:179–184

Numan-M. and Numan-M J., (1994) Behav-Neurosci. 1994 108: 379–394

Numan, M., (1994) Acta Paediatr Suppl 397: 19–28

Brown et al., (1996) Cell 86: 297–309.

Calamandrei, G. and Keverne, E. B., (1994) Behav-Neurosci. 1994 Feb: 108(1):113–12

What is claimed is:

1. A method of determining whether a compound modulates body weight comprising: a) administering a compound to a knockout mouse whose genome is genetically modified to comprise a disruption of the Peg3 gene, wherein said disruption causes increased body weight in the mouse as compared to wild-type body weight, and b) determining whether the compound modulates the body weight of the mouse, wherein a modulation in the body weight of the mouse indicates the compound modulates body weight.

2. A method of determining whether a compound modulates thermoregulation comprising: a) administering a compound to a knockout mouse whose genome is genetically modified to comprise a disruption of the Peg3 gene, wherein said disruption causes decreased body temperature in the mouse as compared to wild-type body temperature, and b) determining whether the compound modulates the body temperature of the mouse, wherein a modulation in the body temperature of the mouse indicates the compound modulates thermoregulation.

* * * * *